US005207090A

United States Patent [19]

Downing, Jr.

[11] Patent Number: 5,207,090
[45] Date of Patent: May 4, 1993

[54] PARTICLE SENSOR FOR STREAM BED

[76] Inventor: John P. Downing, Jr., 260 Kala Heights Dr., Port Townsend, Wash. 98368

[21] Appl. No.: 674,606

[22] Filed: Mar. 25, 1991

[51] Int. Cl.[5] ..................... G01N 15/06; G01N 15/10
[52] U.S. Cl. .................. 73/61.75; 422/68.1; 422/82.13
[58] Field of Search ................ 73/61 R, 28.01, 24.01, 73/24.03, 170 A, 61.71, 61.75, 61.79, 64.53; 422/68.1, 82.12, 82.13

[56] References Cited

U.S. PATENT DOCUMENTS

| 762,172 | 6/1904 | Kersten | 24/128 |
|---|---|---|---|
| 2,359,292 | 10/1944 | Barnett | 426/299 |
| 2,712,128 | 6/1955 | Woodruff | 340/870.13 |
| 3,287,692 | 11/1966 | Turner | 367/161 |
| 3,447,371 | 6/1969 | Bennin | 73/170 R |
| 3,634,885 | 1/1972 | Barkley | 340/573 |
| 3,660,817 | 5/1972 | Abrams | 340/908 |
| 3,906,780 | 9/1975 | Baldwin | 73/61 R |
| 4,096,752 | 6/1978 | Tonnelli | 73/431 |
| 4,114,063 | 9/1978 | Nelkin et al. | 310/334 |
| 4,131,815 | 12/1978 | Boatright | 310/323 |
| 4,225,803 | 9/1980 | Goof | 310/323 |
| 4,480,323 | 10/1984 | Page | 367/131 |
| 4,653,034 | 3/1987 | Hoover et al. | 367/131 |
| 4,837,959 | 6/1989 | Celico | 40/584 |

OTHER PUBLICATIONS

Downing, John P., "Particle Counter for Sediment Transport Studies", Nov. 1981, *Journal of the Hydraulics Division*, ASCE, vol. 107, No. HY11, pp. 1455-1465.

*Primary Examiner*—Tom Noland
*Assistant Examiner*—Rose M. Finley
*Attorney, Agent, or Firm*—Donald W. Marks

[57] ABSTRACT

A sensor for detecting particle flux in a stream has a hollow armored housing enclosing a vibration transducer coupled to the housing for detecting particles impinging on the housing. Also enclosed in the housing is a data logging and control unit for recording particle flux for later retrieval. An ultrasonic acoustic beacon for signalling the condition of the sensor and for indicating the position of the sensor in the event of displacement is also mounted on the sensor. Additionally a brightly colored long buoyant pennant is attached for enabling visual relocation of a displaced sensor.

21 Claims, 10 Drawing Sheets

PARTICLE SENSOR FOR STREAM BED

TECHNICAL FIELD

The invention relates to sensors for measuring the flux or number of solid particles moving past a sensing station by detecting vibrations produced when the particles impinge on the sensor. The particles are carried by a moving fluid such as water, petroleum, or other liquids, or by a mechanical system such as a conveyor belt.

BACKGROUND ART

The prior art, as exemplified in U.S. Pat. Nos. 4,114,063 and 4,131,815 and a publication by John P. Downing, "Particle Counter for Sediment Transport Studies," *Journal of Hydraulics Division, Proceedings of the American Society of Civil Engineers*, ASCE, Vol. 107, No. HY11, Nov. 1981, pages 1455-1465, contains sensors for measuring the flux of moving solid particles by sensing the vibrations produced when the particles impinge upon a stationary target. The vibrations produced by such particle impacts, pings, are damped mechanical oscillations which are converted to electrical signals by an electromechanical transducer, such as ceramic piezoelectric elements, coupled to the target. The transducer signals are amplified, filtered and detected to produce pulses which are counted over predetermined time periods. These counts which correspond to the particle flux can be transmitted or recorded for later recovery. The above U.S. Pat. No. 4,114,063 uses a bandpass range from 10 kHz to 1 mHz; the above Downing publication uses a much narrower bandpass centered at 100 kHz; and the U.S. Pat. No. 4,131,815 uses a resonant frequency in the range of 700 kHz.

The ping rates or counts of detected oscillation events provide a direct in situ measurement of particle-mass flux when the effective cross section (ECD) of the target, the counting efficiency (CE), mean particle diameter, and particle density are known The ECD is the cross-sectional area, including the sensor cross-section, over which a particle has a high probability, say 0.95, of being detected if it passes through that area. The ECD is usually larger than the cross-sectional area of the sensor because grazing impacts can produce detectable pings. Counting efficiency equals (counts detected/actual impacts) $\times 100\%$. Because ECD and CE are difficult to calculate from basic principles of shock and vibration, they are rarely determined explicitly. Instead, a calibration factor is empirically established for relating ping rates to particle-number flux. The calibration factor implicitly contains the product, ECD$\times$CE. When it is multiplied by the ping rate, in counts per second, the particle-number flux, in particles per unit area per unit time is obtained.

One major problem in applications of particle sensors is the abrasive, acoustically noisy, and destructive nature of the media being sensed. Large particles, whether transported in fluids or by mechanical conveyors, have huge destructive action resulting from shock loads. Other causes of damage which shorten the mean time to failure of sensors include, persistent low-energy vibration and fatigue, corrosion by fluids, and bending loads imparted by very large objects, such as trees carried by flooding rivers or streams. To survive in hostile environments, a sensor must be armored and constructed to sustain very large loads without failure.

Another problem concerns collecting and retaining data from the particle sensor. Prior art techniques of connecting sensors to cables, to telemetry apparatus, or to recording devices, are generally unsuitable for hostile environments such as streams where conditions can readily cause failure of the cabling.

In monitoring gravel transport in streams, it is rarely convenient, and frequently impossible, for an operator to be present at all times when measurements are required. Rapid changes in stream condition, such as caused by storms and high water, can produce major changes in the geometry of a gravel stream bed. Point bars can be moved several tens of meters in a few hours, burying a sensor in a low-lying portion of the stream in gravel deposits. A sensor can be displaced tens of meters downstream. Finding the location of a buried and/or displaced sensor can be difficult.

SUMMARY OF INVENTION

In a first aspect, the invention is summarized in a particle sensor including a hollow sealed housing formed from a vibration-transmitting structural material which is resistant to mechanical failure from particle impingement and detrimental environmental conditions, an electro-mechanical transducer contained within the housing and mechanically coupled to the housing for converting vibrations of the housing to electrical signals, and an electronic circuit contained in the housing and electrically coupled to the electro-mechanical transducer for detecting oscillatory events in the electrical signals corresponding to particle impingement.

In a second aspect, the invention is summarized in a sensor including an acoustic beacon mounted on a housing formed from a material which is resistant to mechanical failure and detrimental environmental conditions when placed vertically in a stream with a bottom end of the housing embedded in a bed of the stream. One or more sensors are contained within the housing for sensing stream conditions which are recorded by a recorder responding to electronic circuits contained in the housing and electrically coupled to the sensors.

In a third aspect the invention is summarized in a sensor including a long brightly colored buoyant pennant attached to a tubular sealed housing formed from a material which is resistant to mechanical failure and detrimental environmental conditions when placed vertically in a stream with a bottom end of the housing embedded in a bed of the stream. Sensing means is contained within the housing for sensing one or more conditions of the stream to generate electrical signals which are applied by an electronic circuit contained in the housing to a recorder contained within the housing. The pennant aids visual relocation when the sensor is displaced.

One object of the invention is to construct an improved sensor for detecting movement of large heavy particles and for withstanding the punishment given by such particles.

Another object is to construct a sensor that can be installed in a stream and readily relocated in the event that the sensor is displaced.

It is a further object of the invention to construct a sensor which does not require connection to external transmission wires and equipment while monitoring conditions of streams.

One advantage of the invention is that a protective housing enclosing particle impingement sensing equipment also serves as a sensing element.

Another advantage of the invention is that a sensor for detecting stream conditions includes an acoustic beacon which can signal conditions of the sensor as well as providing a signal that can be used to locate the sensor if displaced.

Still another advantage is that a brightly colored buoyant streamer attached a sensor enables the sensor to be more easily located when displaced downstream.

One additional feature of the invention is the location of batteries in the middle section of a vertical pipe housing having its lower end embedded in a stream so that bending of the pipe by impingement of a large object does not damage expensive sensing equipment mounted in one or both ends of the housing.

A further feature of the invention is the provision of separate battery packs for beacon driving and sensing equipment in a sensor so that exhaustion of the beacon power does not result in loss of data.

Other objects, advantages and features of the invention will be apparent from the following description of the preferred embodiments taken in conjunction with the accompanying drawings.

DESCRIPTION OF THE PREFERRED EMBODIMENT(S)

Figure 1:
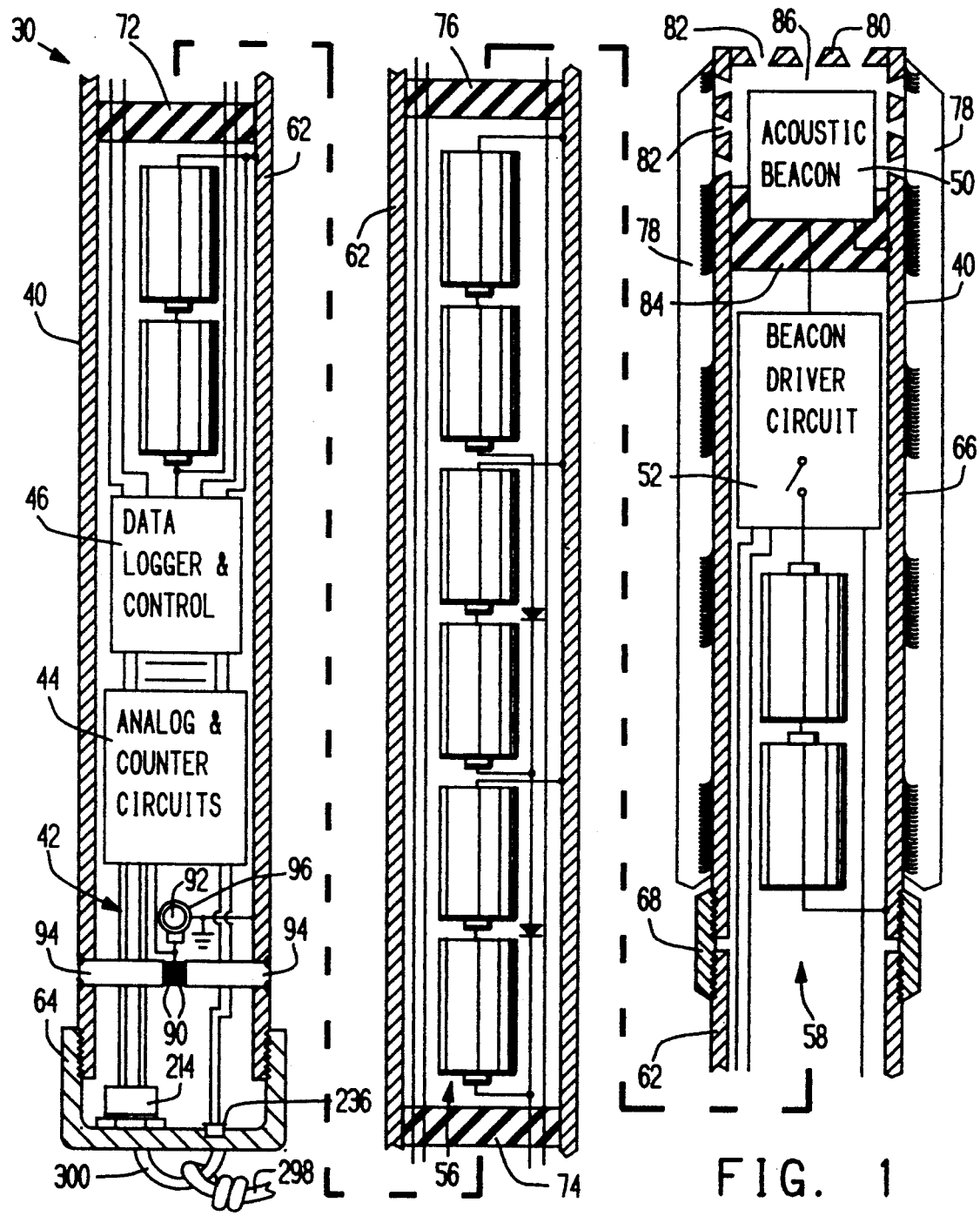
FIG. 1 is diagrammatic elevational section view of a large particle flux sensor constructed in accordance with the invention and broken into vertical segments to fit in the drawing.

As shown in FIG. 1, one embodiment of the invention is a particle flux sensor, indicated generally at 30, which has a strong sealed hollow vibration transmitting housing 40. A transducer indicated generally at 42 is mounted within the housing 40 and is mechanically coupled to the housing to generate electrical signals from vibrations produced in the housing by particles impinging upon the housing. The electrical signals are applied to an analog and counter circuit 44 which filters and detects the number of particle impingements. The counts of particles are recorded in a data logger and control unit 46 contained in the housing for subsequently being read out by conventional computer techniques The sensor 30 also includes an acoustic beacon device 50 which is operated by a beacon driver circuit 52. The beacon is operated periodically, such as for about 10 seconds during every minute, to generate acoustic signals indicating sensor conditions as well as providing a means for locating the position of the sensor in the event it becomes displaced downstream during a storm or other high water condition. One suitable beacon is a DUKANE NA-Series underwater beacon which includes a 37 kHz transmitter.

Batteries, such as pluralities of batteries indicated generally at 56 and 58 for the vibration sensing and beacon circuits, respectively, are suitably mounted in the housing 40 for providing power. Separate batteries 56 for operating the sensing and recording circuits prevent loss of data when the beacon exhausts the batteries 58. Suitable batteries include lithium chloride batteries or other types of batteries or battery packs producing suitable output voltage and power as required by the circuitry.

The sensor 30 is applicable to many industrial, manufacturing, and scientific processes and apparatus where moving particles such as aggregates, large ball bearings, metal fragments, and the like need to be sensed. One industrial application is to measure how uniformly granular material is delivered by a conveyor belt for quality and process control purposes. A possible manufacturing application is to detect large metal fragments or other particles in pipes carrying petroleum products or other bulk liquids. The sensor can be connected to operate valve actuators and/or alarms to stop or divert fluid flow and/or to warn operators of such conditions. Still another application is to employ the sensor in the intakes of cooling water or water treatment plants to warn operators of excessive incoming particles.

Figure 2:
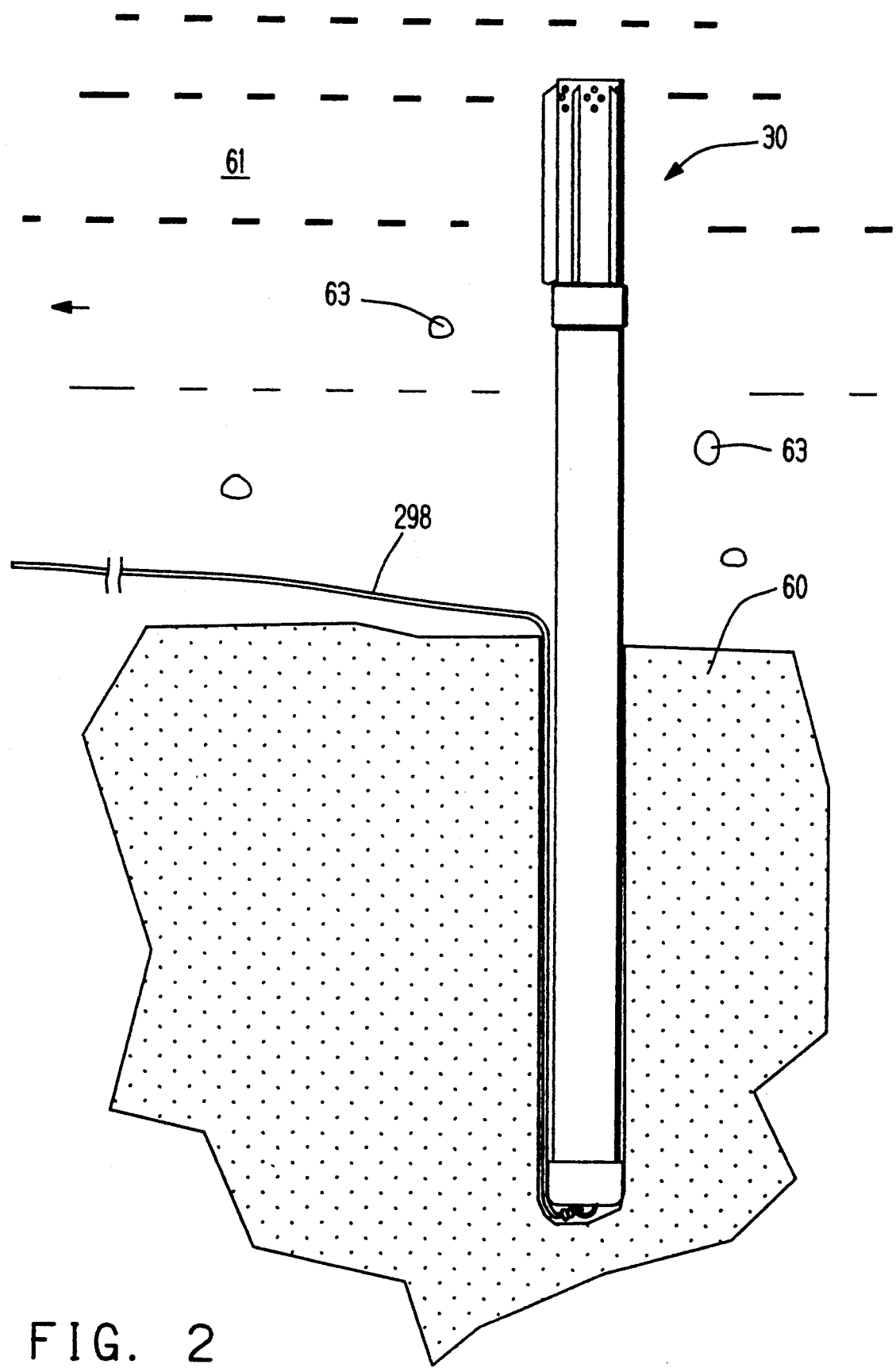
FIG. 2 is an elevation view of the particle sensor of FIG. 1 placed in a stream.

As shown in FIG. 2, the sensor 30 finds particular utility by having its bottom end embedded in a stream bed 60 with its top end projecting upward into a stream 61 for measuring movement of large particles such as gravel 63. These particles are generally greater that $\frac{1}{2}$ inch (1 cm) in diameter and have a specific gravity greater than 2.0. Measuring particle movement is useful in stream management. Gravel-bedded streams provide spawning habitat for anadromous fish with commercial and recreational value. Diversions of water flow for irrigation, water supply, and power generation can profoundly affect the quality and area of spawning habitats. Environmental managers are required by FERC Regulations (CFR Chapter 18) to allocate water resources for their projects in a way that sustains spawning habitat in stream channels. The sensor 30 provides environmental managers with a new method for obtaining continuous, time-registered records of stream level, water temperature, gravel transport, and other optional parameters without being on site or maintaining a data transmission link in a hostile environment.

Impacts of particles on the housing 40 within a body of water produce damped oscillatory vibrations or pings which have a fundamental frequency in the range from about 5 to 15 kHz, for example about 10 kHz, and have durations less than 3 milliseconds. By counting the number of pings produced over selected periods of time and averaging the counts, an average ping rate can be calculated. The ping rate is proportional to the particle flux, particle density, and the sectional area of the sensor exposed in the stream to the impinging particles.

The housing 40, as illustrated in FIG. 1, is in the form of a pipe 62 with a cap 64 threaded onto the bottom. The cap 64 has threaded holes for a pressure sensor 214 and a temperature sensor 236. Additionally one or more holes (not shown) can be provided for a dissolved oxygen sensor (not shown), a pH sensor (not shown), a connector (not shown) for coupling the unit to an external transmission line (not shown), and/or many other types of sensors or devices. A top section 66 is mounted on the upper end of the pipe 62 by a threaded coupling 68. The housing 40 is three or four to ten feet (1 to 3.4 meters) in length. It is formed from a structural metal such as stainless steel, steel, aluminum, titanium, or the like. As an example, the pipe 62 and top section 66 can be formed from commercial two inch (5 centimeter) diameter pipe of stainless steel type SS-316 which is four feet (1.3 meters) in length.

The central portion of the housing 40 which contains most of the batteries 56 is sealed by rubber seals 72, 74 and 76 from the rest of the housing. This central portion is the most likely portion to be bent in the event of a large object, such as a tree limb or tree trunk, hitting the sensor. By installing the least expensive items, batteries, in this section, the damage caused by such a collision of a large object with the sensor is minimized.

A plurality of longitudinal reinforcing ribs 78 are welded to the outside of the cylindrical wall of the upper section 66 at five locations evenly spaced about the cylindrical wall. An example of suitable ribs are metal strips one-fourth inch (6 millimeters) thick, one-half inch (12millimeters) wide, and twelve inches (31 centimeters) long. The upper end of the section 66, including the welded top end wall 80, is perforated to conduct the acoustic waves from the beacon 50 to the surrounding water. An example of suitable perforations are one-fourth inch (6 millimeter) counter sunk holes 82 evenly spaced in diamond patterns. A rubber seal 84 seals the top chamber 86 having the perforated walls and containing the acoustic beacon 50 from the rest of the sensor interior. The perforated top chamber 86 permits direct contact of the water with the beacon transducer 50 to provide a greater acoustic energy transfer efficiency while protecting the beacon transducer from being damaged by impinging particles.

The sensing transducer 42 includes two pairs of piezoelectric discs 90 and 92 which are supported between pairs of rods 94 and 96 extending diagonally across the pipe. The support rods 94 are rotated 90° from the support rods 96 so that the sensor detects vibrational modes produced by particle impingement at any angle to the housing wall and at any position in the 360° circumference of the housing 40. Each pair of rods 94 and 96 with the corresponding pair of interposed discs 90 and 92 is inserted through appropriate holes in the wall of the housing and welded in place while the housing wall is distorted or stretched in the direction of the rods being installed so that the elasticity of the housing compresses the discs between the rods upon release of the distortion force. This insures an efficient transduction of vibration to electric signals. An example of suitable sensor transducing elements includes discs made from lead zirconate titanate (PZT), such as Vernitron PZT-5A ceramic discs, or other similar piezoelectric materials.

Figure 3:
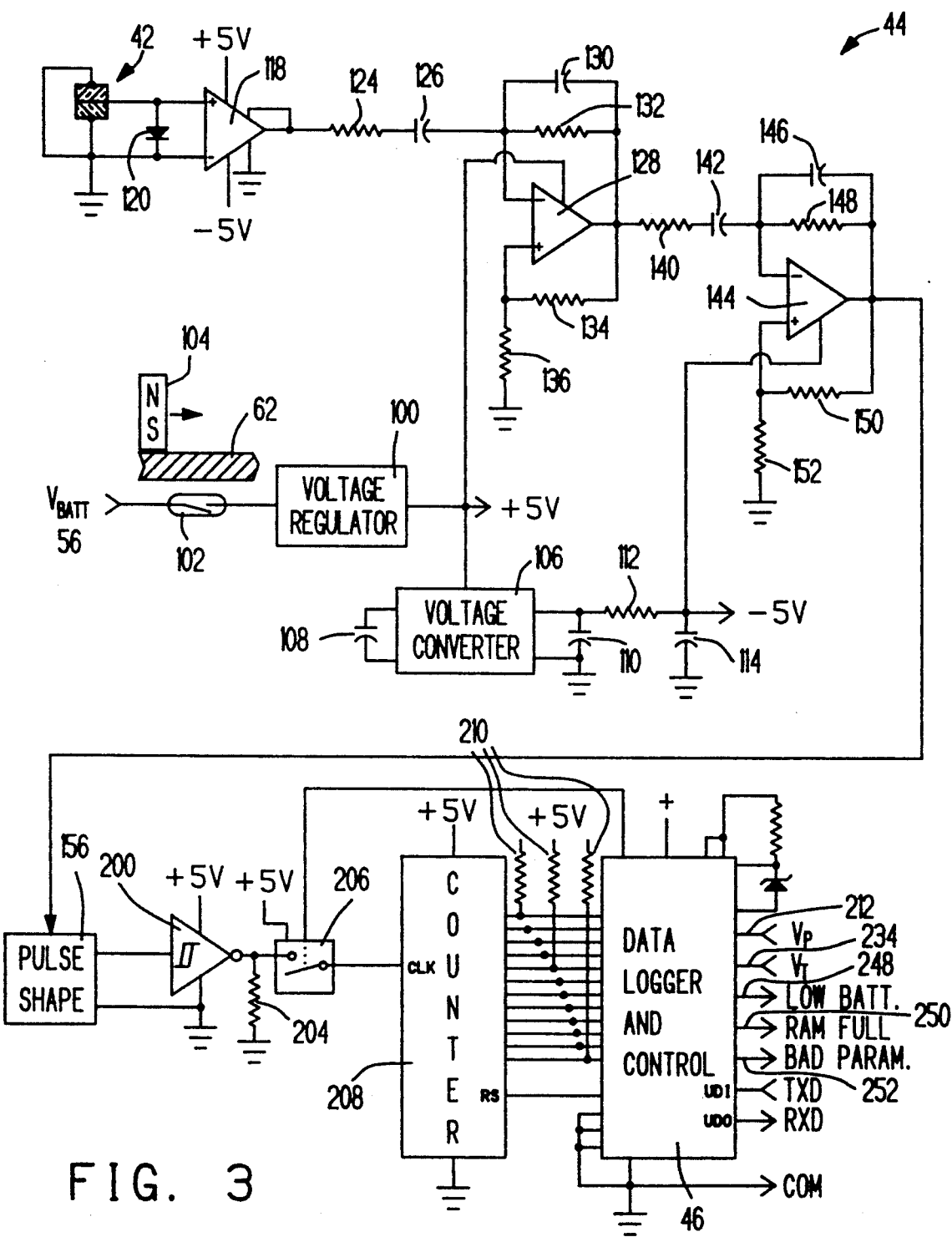
FIG. 3 is an electrical schematic of analog, counter, data logger and control circuits of the sensor of FIG. 1.

As shown in FIG. 3, the analog and counter circuit unit 44 includes a voltage regulator 100 which is connected by a normally open but latching-type magnetic switch 102 to the battery supply 56. The magnetic switch 102 is mounted on or adjacent to the interior surface of the pipe 62 so that the switch can be operated by a magnet 104. The voltage regulator 100 produces the regulated positive voltage required by the circuit. A voltage converter 106 with associated control capacitance 108 is operated by the positive voltage supply to generate a regulated negative voltage as required by the analog portions of the circuitry. This negative voltage is filtered by parallel capacitance 110, series resistance 112 and parallel capacitance 114.

Figure 9:
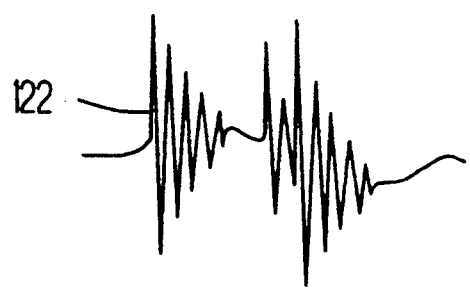
FIG. 9 as a waveform diagram of a typical signal produced from a preamplifier of the circuit of FIG. 3.

The output of the transducer 42 is coupled to the inputs of an amplifier 118. A voltage limiting diode 120 is connected across the amplifier inputs. In FIG. 9, waveform 122 is typical of the output of the amplifier 118 for three successive impingements with the later two overlapping. The output of the amplifier 118 is connected by a series resistance 124 and capacitance 126 to the inverting input of an amplifier 128 across which are connected feedback capacitance 130 and resistance 132. Resistances 134 and 136 provide suitable gain for the amplifier 128. The output of the amplifier 128 is connected by series resistance 140 and capacitance 142 to the inverting input of an amplifier 144. Parallel filter capacitance 146 and resistance 148 and gain resistances 150 and 152 are connected to the amplifier in the same manner as provided for amplifier 128.

Figure 10:
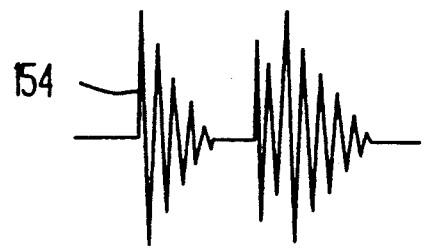
FIG. 10 is a waveform diagram of a typical signal produced from a bandpass filtering portion of the circuit of FIG. 3.

The amplifiers 128 and 144 with their associated series and parallel capacitances and resistances form a band pass filter. The fundamental frequency of the vibrations produced by the particle impacts will vary based upon many complex factors including the acoustic properties of the housing, the transducer, the mounting rods, and the medium in which the sensor is positioned. The optimum band pass frequency is best determined empirically. In an example of one sensor, the bandpass frequencies were selected to range from about 5 to about 15 kHz. The bandpass filter eliminates false readings caused by ambient noise unrelated to the particle impacts. Waveform 154 in FIG. 10 represents the output of the bandpass filter produced by the input signal 122.

Figure 4:
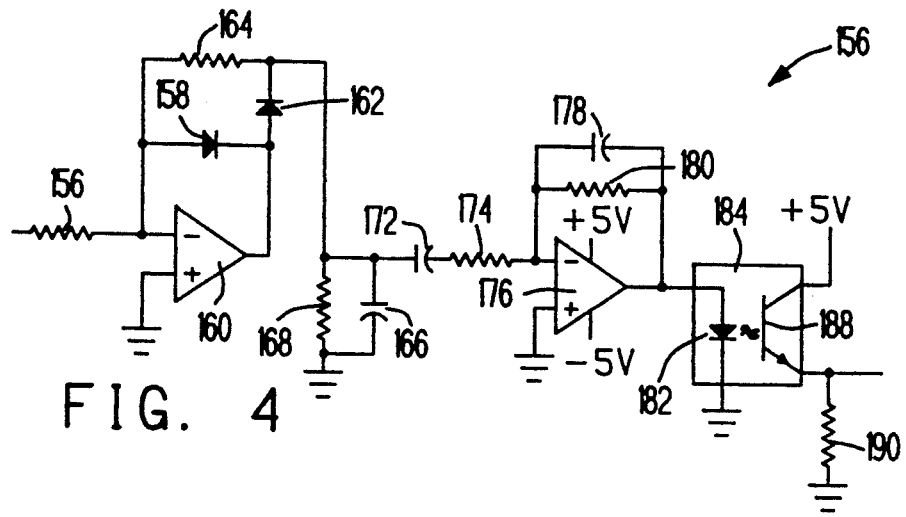
FIG. 4 is an electrical schematic of a pulse shaping circuit of FIG. 3.
Figure 11:
FIG. 11 is a waveform diagram of a typical signal produced from a detecting circuit portion of the pulse shaping circuit of FIGS. 3 and 4.
Figure 12:
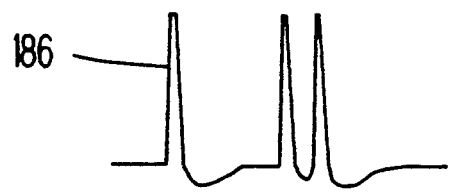
FIG. 12 is a waveform diagram of a typical signal produced from a pulse differentiating circuit portion of the pulse shaping circuit of FIGS. 3 and 4.

From the band pass filter, signals are passed to a pulse shaping circuit 156 which is shown in detail in FIG. 4. Series input resistance 156 applies these signals to a diode 158 and the inverting input of an amplifier 160. The outputs of the amplifier 160 and the diode 158 are connected to a diode 162 which generates a fully rectified output signal. Resistor 164 provides feedback for the amplifier 160. The rectified output is filtered by parallel capacitance 166 and resistance 168. Waveform 170 in FIG. 11 represents the output of the detector circuit formed by the diodes 158 and 162 and the amplifier 160. The detected signal is then differentiated by series capacitance 172 and resistance 174 together with amplifier 176, its associated parallel feedback capacitance 178 and resistance 180, and the diode 182 of an optical isolator 184. Waveform 186 in FIG. 12 shows the pulse output generated by the optical isolator transistor 188 and a resistance 190 from the differentiated signal.

Figure 13:
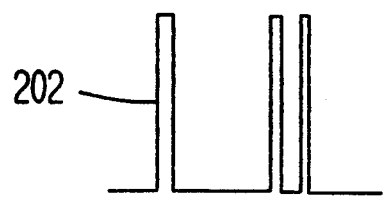
FIG. 13 is a waveform diagram of a typical signal produced from a squaring circuit of FIG. 3.

Referring back to FIG. 3, the differentiated pulse signals from the pulse shaping circuit 156 are applied to a squaring circuit or Schmitt trigger 200. Squared pulses, shown in waveform 202 of FIG. 13, are produced across the output resistance 204 of the squaring circuit and applied to a normally open electronic switch 206 which is controlled by the data logger and control unit 46. The output of the switch is connected to the clock or counting input of a counter 208. The counter has its reset input connected to an output of the data logger and control unit 46. In one example, the counter 208 is a fourteen-bit CMOS binary counter. The least significant and eleven most significant bit outputs of the counter 208 are connected to data inputs of the data logger and control unit 46. Resistances 210 (only three shown) bias the data inputs high.

The data logging and control unit 46 is a commercial miniature microprocessor-controlled data logger, such as an Onset Computer Corporation Tattletale Model 5 data logger These types of units contain adequate memory (RAM) which can be of a non-volatile but writable type to record data records. Additionally they contain analog inputs along with digital inputs/outputs. Further the units have analog-to-digital converters for converting analog values on the analog inputs to digital values along with battery voltage reading circuitry. Conventional serial transmitting and receiving circuitry is included for being connected by outputs TXD and RXD to transfer lines to an external computer (not shown) and printer (not shown) to download and print the stored data. In the disclosed unit 46, two analog inputs are used for measuring pressure and temperature, twelve digital I/O lines are used for receiving ping counts from the counter 208, one I/O line is used to reset the counter, and three I/O lines are used to control the beacon driver circuit.

Figure 6:
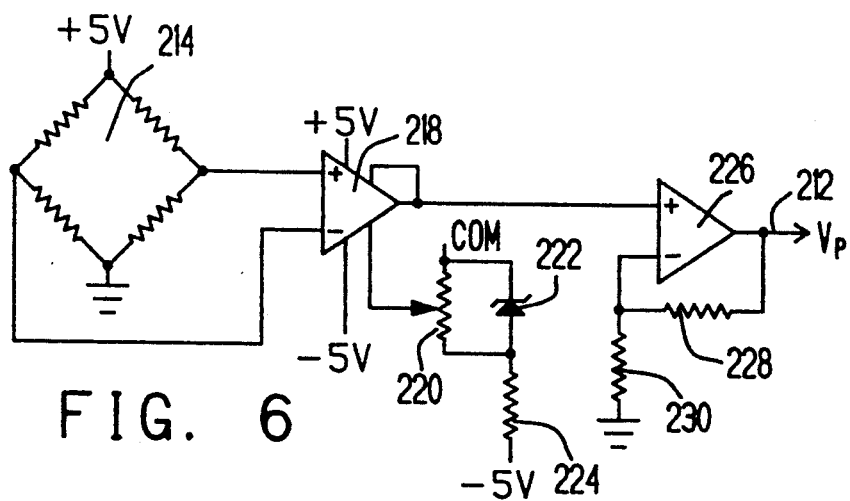
FIG. 6 is an electrical schematic of a pressure sensing circuit included in the apparatus of FIG. 1.

The unit 46 has a $V_P$ input 212 from the pressure sensing circuit shown in FIG. 6. Any rugged, all-media, solid-state absolute pressure transducer can be used to measure the hydrostatic or fluid pressure. In FIG. 6 the pressure sensor is a bridge-type pressure sensing transducer 214, such as NOVA No. NPI-19A-201-AH0, which has positive and ground voltage inputs, and which has outputs connected to the inputs of an amplifier 218. A pressure set point is determined by potentiometer 220 which is connected across zener diode 222 and in series with resistance 224 to the negative voltage. The output of the amplifier 218 is connected to the input of an amplifier 226 with feedback resistances 228 and 230. The output of the amplifier 218 drives the line 212.

Figure 7:
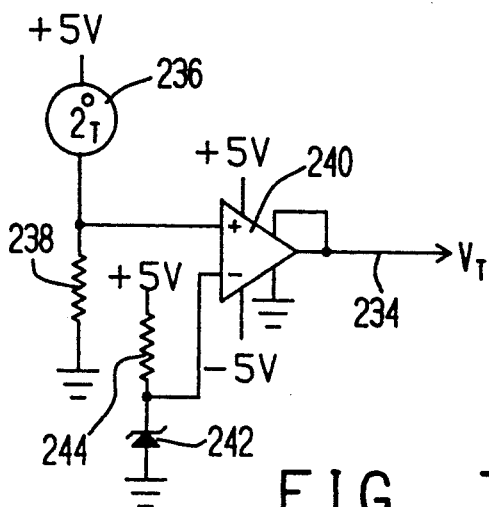
FIG. 7 is an electrical schematic of a temperature sensing circuit included in the apparatus of FIG. 1.

A $V_T$ input 234 to the unit 46 in FIG. 3 is connected to a temperature sensing circuit in FIG. 7. Suitable temperature sensing elements include linearized thermistors such as those manufactured by Y.S.I. and Thermonics, PTC thermistors such those manufactured by Midwest Components and Katema Rodan, and linear T.C. zener diodes such as those manufactured by National Semiconductor and Analog Devices The temperature sensing element 236 in FIG. 7 is an Analog Devices AD590 in series with a resistor 238. An amplifier 240 has one input connected to the temperature sensor and its other input connected to a reference voltage from zener diode 242 connected in series with resistor 244. The amplifier 240 drives the line 234.

Figure 5:
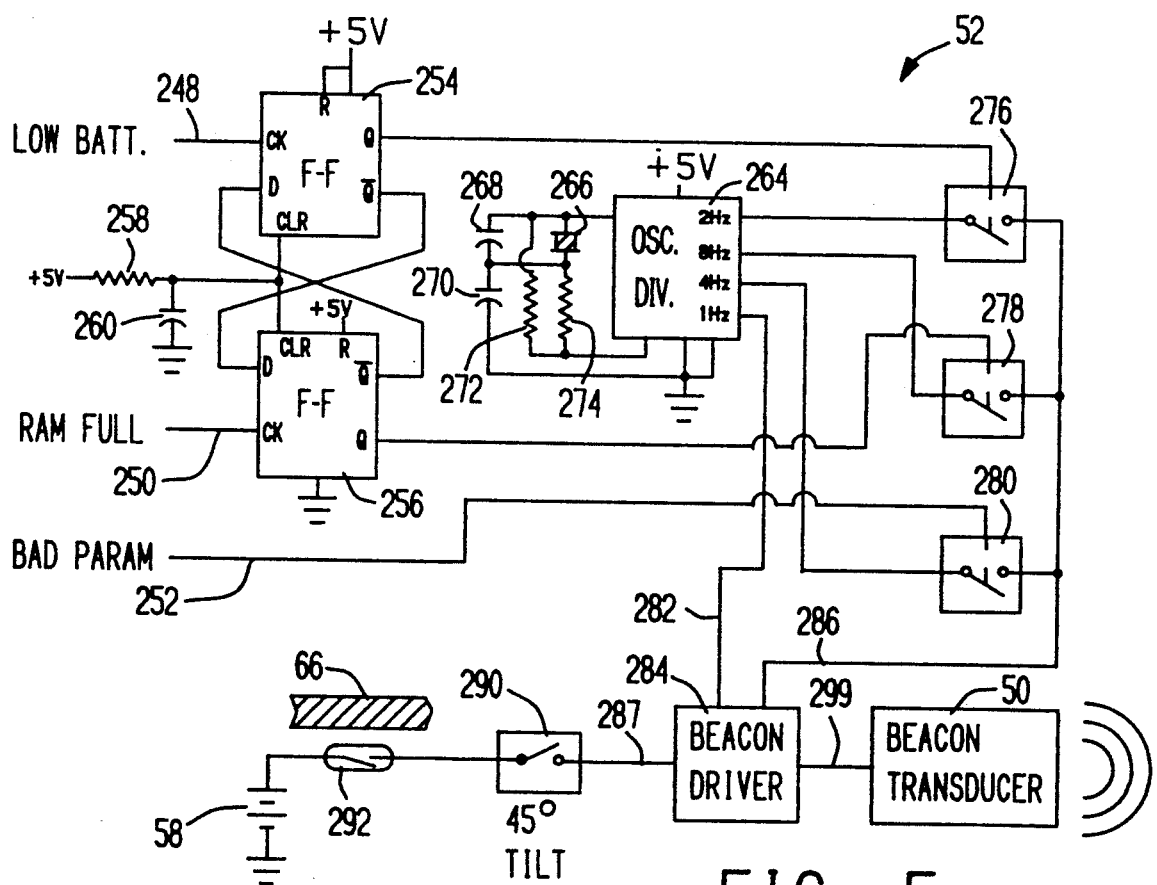
FIG. 5 is an electrical schematic of a beacon driver circuit of the sensor of FIG. 1.

Outputs of the data logger and control unit 46 in FIG. 3 include LOW BATT output 248, RAM FULL output 250 and BAD PARAM output 252. As shown in FIG. 5, the lines 248 and 250 operate respective flip-flops 254 and 256. The inverted outputs of the flip-flops 254 and 256 are connected to the data inputs of the respective other flip-flop so that the first flip-flop to operate prevents operation of the other flip-flop. An initializing circuit of positive biased series resistance 258 and parallel capacitor 260 is connected to the clear inputs of the flip-flops 254 and 256 to initially reset the flip-flops when the power is applied to the circuit. An oscillator/divider unit 264 controlled by a crystal 266, capacitors 268 and 270 and resistors 272 and 274 produces output signals of one Hertz, two Hertz, four Hertz and eight Hertz. Switch 276 operated by the flip-flop 254, switch 278 operated by the flip-flop 256 and switch 280 operated by the signal on line 252 selectively connect the respective two-Hertz signal, eight-Hertz signal and four-Hertz signal to a line 282 connected to the beacon driver 284 The oscillator/divider 264 also generates a one-Hertz signal on line 286.

Figure 8:
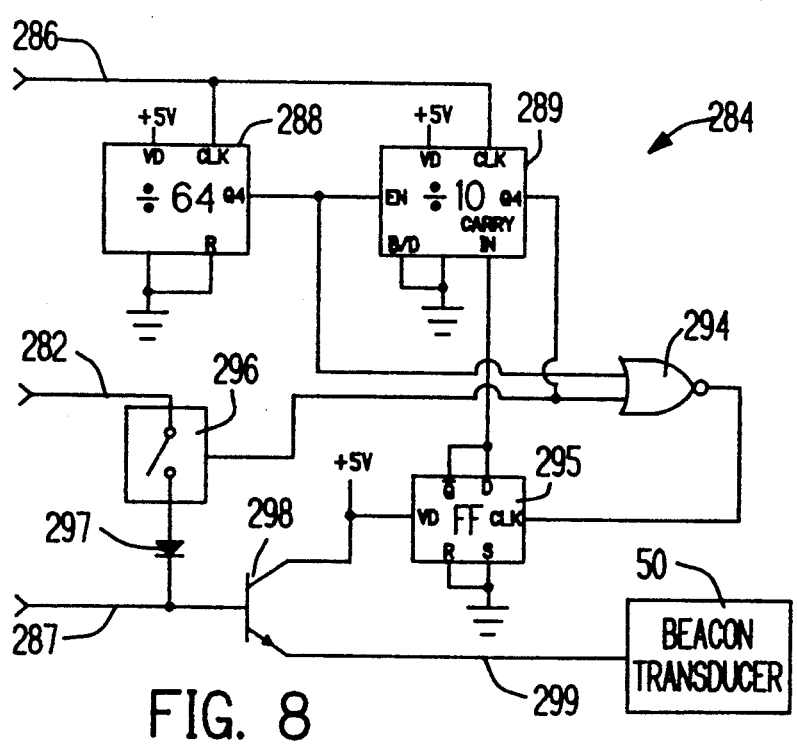
FIG. 8 is an electrical schematic of a beacon driver circuit of the sensor circuit in FIGS. 1 and 5.

The beacon driver circuit 284, as shown in FIG. 8, includes a divide-by-sixty-four counter 288 and a decade counter or divider 289 connected to the one-hertz oscillator line 286. The output of the counter 288 is connected to an enable input of the counter 289 and to one input of NOR gate 294 which receives its second input from the output of the counter 289. The output of the NOR gate 294 is connected to the clock input of a D-type flip-flop 295 which has its inverted output connected to it data input and to a carry-in or second enabling input of the counter 289. The output of the counter 289 operates a normally open electronic switch 296 which is connected in series with the line 282 and a diode 297 to the base of a transistor switch 298 which operates the beacon transducer 50 over line 299.

Figure 17:
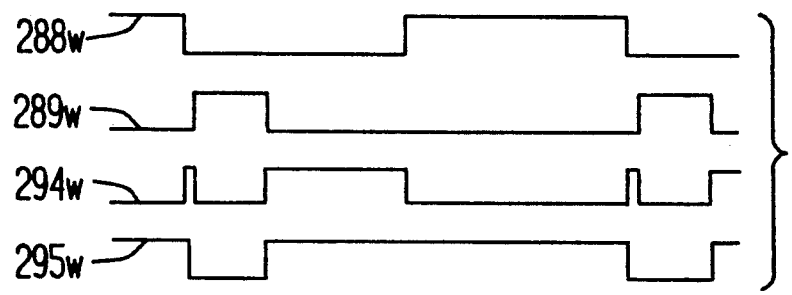
FIG. 17 is diagram of four waveforms generated in portions of the beacon driver circuit of FIG. 8.

In operation of the beacon driver circuit, the waveforms 288w, 289w, 294w and 295w of FIG. 17 are produced by the counter 288, the counter 289, the NOR gate 294 and the flip-flop 295, respectively. The waveform 288w goes low after the counter 288 counts sixty-four clock pulses to cause the output 294w of NOR gate 294 to go high. This toggles the flip-flop 295 to render the waveform 295w low which together with the waveform 288w enables the counter 289. The output 289w of the counter 289 goes high for ten cycles of the one-Hertz signal on line 286 rendering the output 294w of the NOR gate 294 low. When the waveform 289w then goes low the output 294w of NOR gate returns to the high state which again toggles flip-flop 295 to render waveform 295w high to disable the counter 289 until the counter 288 completes another count of sixty-four, one-Hertz cycles to start another cycle.

Any two-Hertz, four-Hertz or eight-Hertz signal applied to line 282 by the operation of one of the respective switches 276, 278 and 280 in FIG. 5 is passed by the switch 296, FIG. 8, to the transistor 298 during the short time (ten second interval) that the waveform 289w is high. During the remainder of the sixty-four count period of counter 288, the switch 296 is open and the transistor 298 is off. Thus the beacon 50 is only intermittently operated to conserve battery power when indicating a condition detected by the data logger and control unit 46.

The sensor also includes a tilt switch 290 which is in series with a normally open but latchable magnetic switch 292 between the battery supply 58 and the input of the beacon driver 284. The sensor 30 detects and counts impacts while oriented 90°±45° to particle trajectories. When the angle between the sensor and particle trajectories is less than 45°, the effective cross section (ECD) and the counting efficiency (CE) diminish sharply, and the calibration factor becomes unknown. The tilt switch 290 is a mercury switch which detects when the sensor 30 is no longer oriented within 45° of vertical or its upper end is bent more than 45°. The magnetic switch 292 is similar to and located next to the magnetic switch 102 of FIG. 3. The magnetic switch 292 locks out operation of the beacon by the tilt switch 290 until the magnetic switch is closed by a magnet. This enables the sensor to be transported or stored in a horizontal position until ready to be employed.

The output of the tilt switch 290 is connected by line 287 to the transistor 298 in the beacon driver 284, FIG. 8, to continuously operate the beacon transducer 50 producing continuous acoustic signals until the batteries 58 are exhausted or the sensor unit is recovered from the stream. This provides an operator with an acoustic signal to locate the sensor should it be washed downstream during high water.

Preferably the beacon 50 generates ultrasonic signals, signals greater than 20 kHz, which are well above the ambient noise produced by streams (100 to 500 Hz). For example the beacon transducer 50 can generate 37 kHz acoustic signals A conventional directional microphone (not shown) or hydrophone (not shown) can be used to pick up the ultrasonic signals which can then be heterodyned to an audible frequency in the range from 100 to 6000 Hz. This audible signals are then applied to a speaker (not shown) or ear phones (not shown) to be heard by an operator. One suitable beacon locator is DUKANE Model 42A12B ultrasonic test set with Model 810385A hydrophone.

Some or all of the printed circuits are formed on a flexible substrate such as ACME PCB Hi Impedance mylar so as to tolerate moderate bending.

Another aid to location of sensors which have been displaced by abnormal stream flow is a long brightly colored pennant 298 shown in FIGS. 1 and 2. This pennant is a high strength, buoyant line attached to a ring or loop 300 mounted on the cap 64. Exposed sections of the pennant will float up above the stream bed and be visible from the surface. A buried sensor can be located when only part of the pennant is exposed at the surface. The pennant 298 can have colored bands placed in a manner to indicate the direction of the sensor so that a buried sensor can be recovered by digging through the gravel in the direction indicated by the colored bands. For example, the pennant can be a yellow polypropylene rope which is four to ten meters in length.

Figure 14:
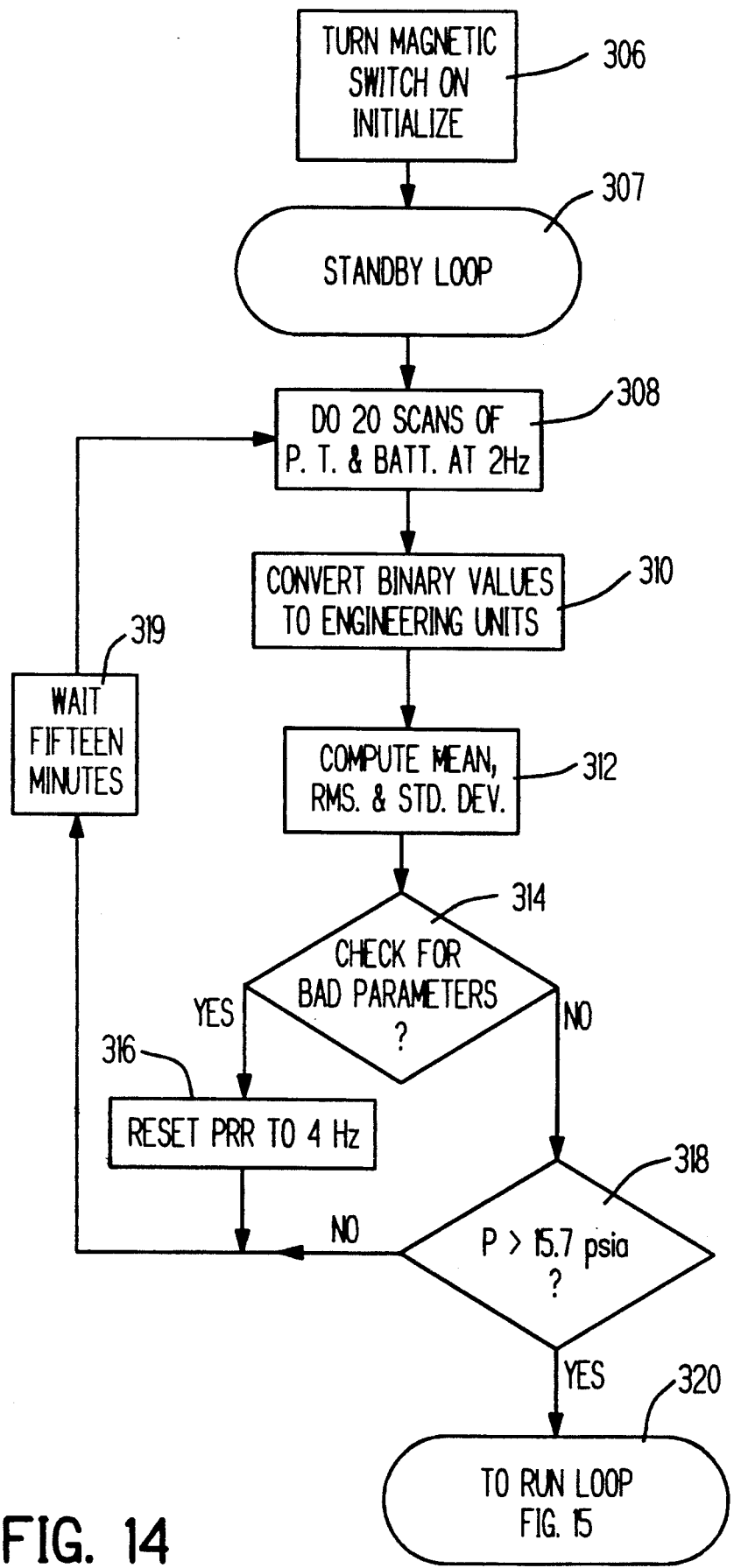
FIG. 14 is a step diagram of a first portion of a program used in the data logger and control unit of FIG. 3.

The operating program for the data logging and control unit 46 is contained in a programmable read only memory (PROM). This program, as shown in FIG. 14, is started when the power is turned on by operation of the magnetic switch 102 in step 306. Any required initialization procedures are performed at this time. Then the program enters the standby loop at point 307 and performs step 308 in which twenty readings of the pressure, temperature and battery voltage are preformed and temporarily stored These binary values are converted to engineering units in step 310 and the mean, the root mean square and the standard deviation values are computed in step 312. In step 314, the program checks the computed values for being outside of acceptable ranges. If a parameter is outside of an acceptable range, there is a failure of a sensing element and the program branches to step 316 where the BAD PARAM output line 252, FIGS. 3 and 5, is rendered high to operate switch 280 and drive the beacon 50 with a four Hz signal to indicate the failure. From step 316 the program returns through fifteen minute wait step 319 to step 308. If step 314 is false, the program proceeds to step 318 where the computed pressure is compared to a value of 15.7 psia (108 kPa). Pressures less than or equal to this value indicate that the sensor is not installed in a stream, and the program returns through fifteen minute wait step 319 to the step 308. If the pressure is greater than 15.7 psia (108 kPa), the program enters the run loop at point 320.

Figure 15:
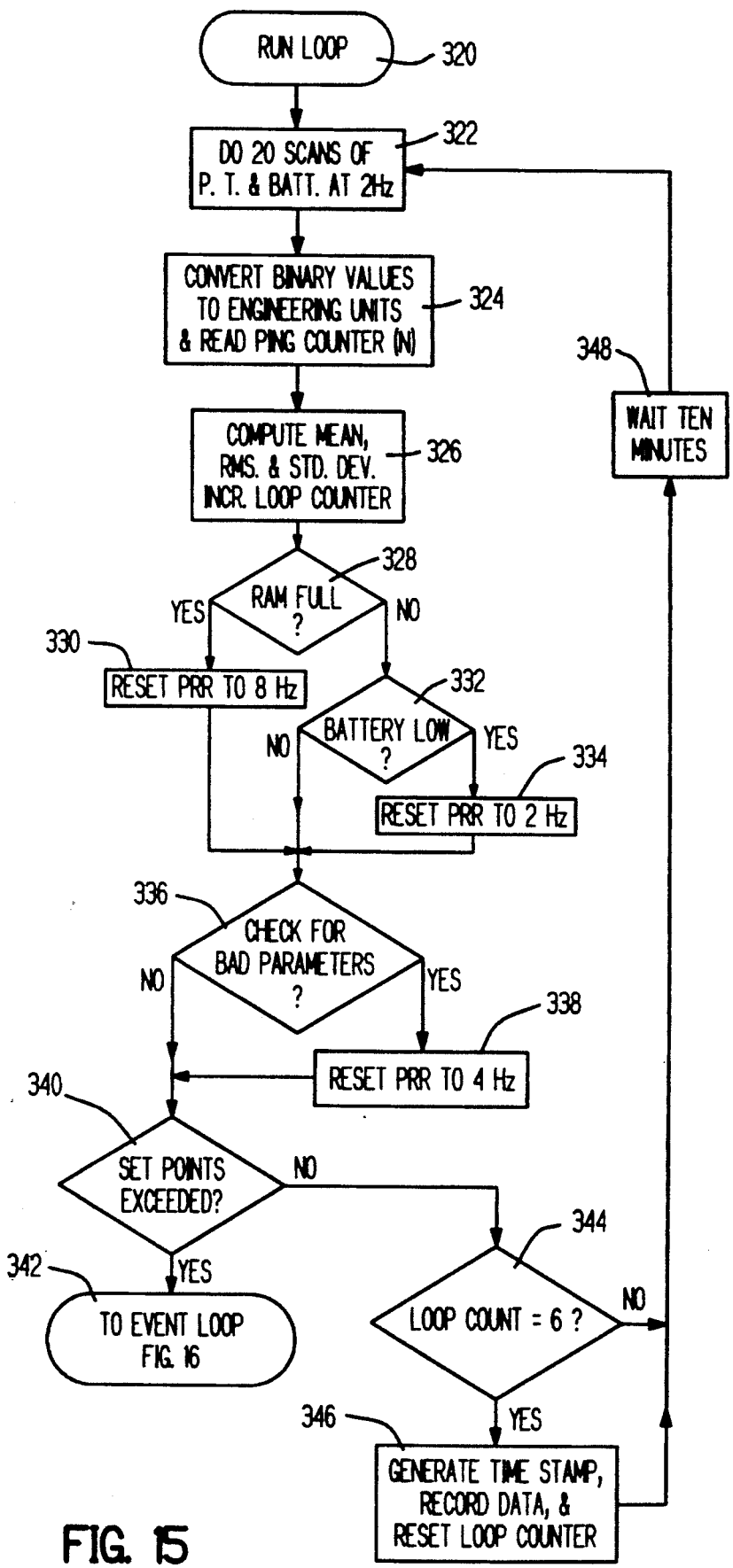
FIG. 15 is a step diagram of a second portion of a program used in the data logger and control unit of FIG. 3.

As shown in FIG. 15, the first step 322 of the run loop performs twenty readings of pressure, temperature and battery voltage and places the readings in temporary storage. In the next step 324, the binary readings from step 322 are converted to engineering units and the ping counter 208, FIG. 3, is read and reset. Next the mean, the root mean square and the standard deviation values are calculated in step 326 from the temporarily stored readings. A loop count is also incremented in step 326. Whether adequate RAM is available for storage of an additional record is queried in step 328. If RAM is full, the line 250 is rendered high in step 330 to operate flip-flop 256 and close switch 278 which operates the beacon 50 at eight Hz. Similarly in step 332 the battery voltage is queried. If the battery voltage is low, the line 248 is rendered high in step 334 to close switch 276 which operates the beacon 50 at two Hz. From steps 330 and 334 and from step 332 if false, the program proceeds to step 336 where the sensed values are checked for being in acceptable ranges. If a bad parameter is found, the program branches to step 338 where the line 252 is rendered high to pulse the beacon at four Hz. From step 338 or step 336 if false, the program proceeds to step 340 to determine if the sensed values exceed any set points. One set point is a normal maximum value for the number of pings detected. Another set point could be a normal maximum pressure. If a set point is exceeded, the program branches to point 342 and an event loop. Otherwise the program goes to step 344 where the loop count is compared to six. If the loop count is equal to six, step 346 enters a record in the RAM by recording the time and computed values, and the loop count is reset to zero. This conserves the use of RAM so that less recording RAM is used during normal conditions leaving more RAM for recording data of abnormal conditions. From step 346 or step 344 if false, the program returns via ten minute wait step 348 to step 322.

Figure 16:
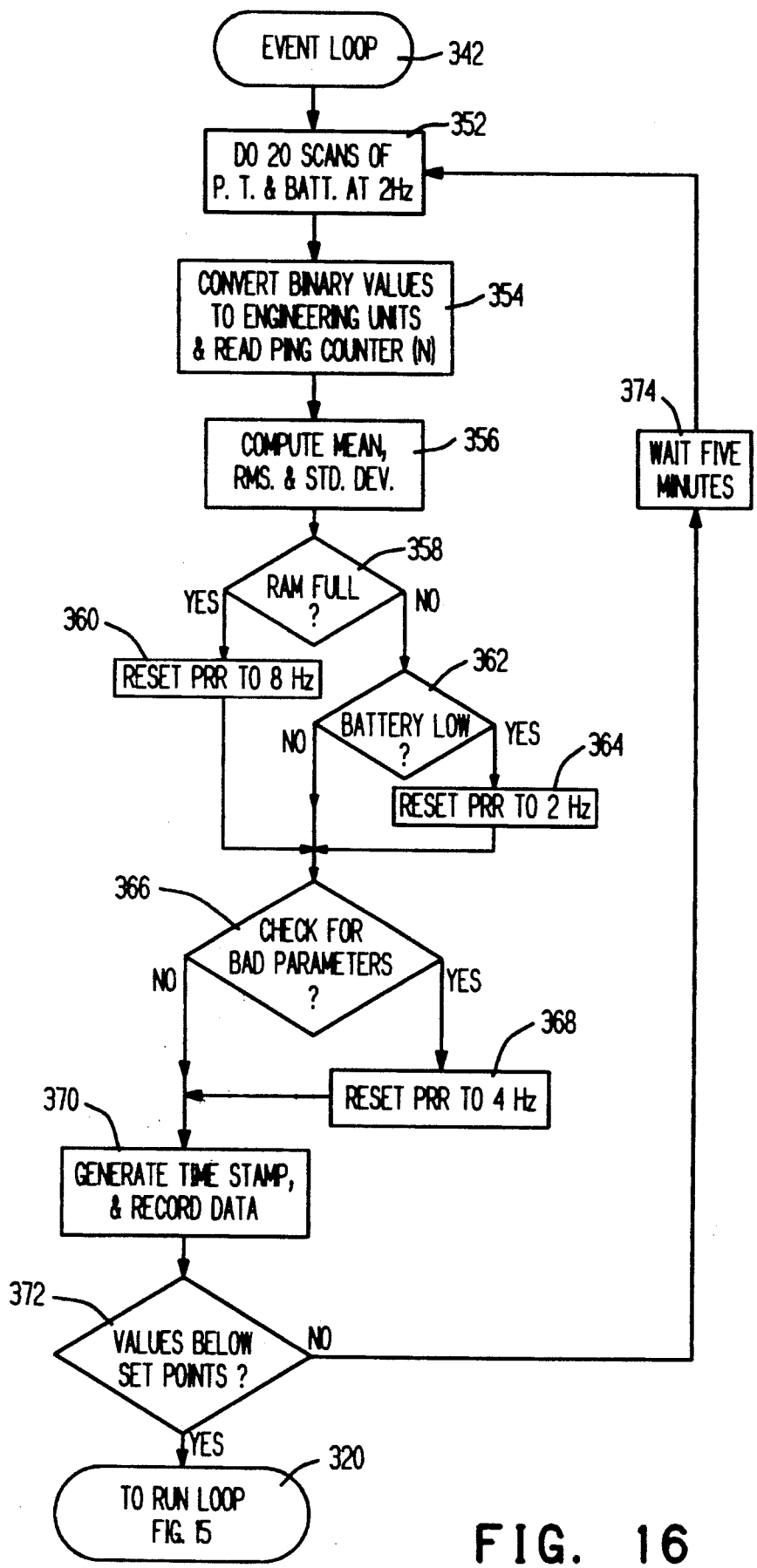
FIG. 16 is a step diagram of a third portion of a program used in the data logger and control unit of FIG. 3.

The event loop, as illustrated in FIG. 16, includes steps 352, 354, 356, 358, 360, 362, 364, 366 and 368 which are substantially similar to steps 322, 324, 326, 328, 330, 332, 334, 336 and 338 in the run loop of FIG. 15, except that step 356 does not increment any loop count. However in the next step 370, the time and data are recorded during every loop cycle as compared to being recorded only every sixth cycle in the run loop. In step 372, the measured values are compared to set points to determine if the conditions indicating an abnormal event still exist. If the values have returned to normal the program branches back to point 320 and the beginning of the run loop Otherwise the program recycles through five minute wait step 374 to step 352 to continue recording data.

During the wait steps 319, 348 and 374, the unit 46 goes to sleep to conserve battery energy. These wait periods provide appropriate intervals between sensing cycles so that the sensed data provides a good profile of changing stream conditions.

Figure 18:
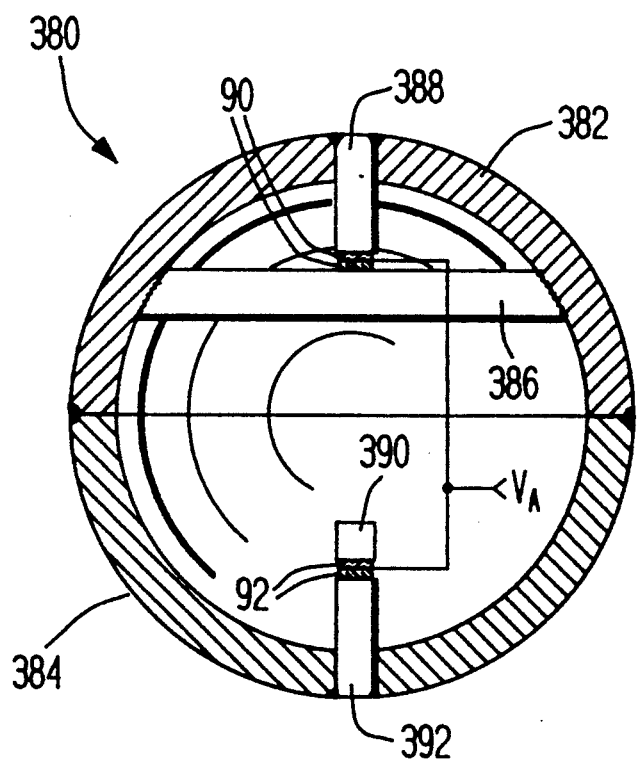
FIG. 18 is an sectional view of a modified particle sensor in accordance with the invention.

A variation of the sensor is illustrated in FIG. 18 wherein the sensing housing is in the form of a hollow sphere indicated generally at 380. The sphere is formed from two hemispheres 382 and 384 sealed together The piezoelectric elements 90 are held in compression between a cross member 386 and the end of a rod 388 in the hemisphere 382 while the elements 92 are held in compression between a cross member 390 and the end of a rod 392 in the hemisphere 384. The cross members 386 and 390 are oriented at 90° relative to each other while the rods 388 and 392 are coaxial so that the transducer responds to impingements at all positions and angles on the sphere.

Since many variations, modifications and changes in detail may be made to the above described embodiments, it is intended that the foregoing description and accompanying drawings be interpreted as only illustrative of the disclosed embodiments and not as limiting the invention defined in the following claims.

What is claimed is:

1. A particle sensor comprising:
    a hollow sealed housing formed from a vibration-transmitting structural material which is resistant to mechanical failure from particle impingement and detrimental environmental conditions when anchored in a stream to a bed of the stream,
    an electro-mechanical transducer contained within the sealed vibration-transmitting housing and mechanically coupled to the housing for converting vibrations of the housing to electrical signals, and
    an electronic circuit contained in the sealed vibration-transmitting housing and electrically coupled to the electromechanical transducer for detecting oscillatory events in the electrical signals corresponding to particle impingement.

2. A particle sensor as claimed in claim 1 including recording means contained in the housing for recording data of the oscillatory events, and battery means contained in the housing for energizing the electronic circuit and the recording means.

3. A particle sensor as claimed in claim 1 wherein the housing is tubular.

4. A particle sensor as claimed in claim 3 wherein the housing is spherical.

5. A particle sensor as claimed in claim 3 wherein the housing is steel, aluminum or titanium.

6. A particle sensor as claimed in claim 2 wherein the recording means is a microprocessor-controlled data logger including non-volatile RAM for storing the data.

7. A particle sensor as claimed in claim 2 including a normally-open, latching-type, magnetic switch connected between the battery means and the electronic circuit within the housing.

8. A particle sensor comprising:
    a tubular sealed housing formed from a vibration-transmitting structural material which is resistant to mechanical failure from particle impingement and detrimental environmental conditions when placed vertically in a stream with a bottom end of the housing embedded in a bed of the stream,
    an electro-mechanical transducer contained within the sealed vibration-transmitting housing and mechanically coupled to the housing for converting vibrations of the housing to electrical signals,
    an electronic circuit contained in the sealed vibration-transmitting housing and electrically coupled to the electromechanical transducer for detecting oscillatory events in the electrical signals corresponding to particle impingement,
    recording means contained within the sealed vibration-transmitting housing and coupled to the electronic circuit for recording data of the oscillatory events, and
    acoustic beacon means mounted on the housing for emitting an acoustic signal.

9. A particle sensor as claimed in claim 8 wherein the acoustic beacon means emits an ultrasonic acoustic signal.

10. A particle sensor as claimed in claim 8 including means contained in the housing the pulsing the acoustic beacon means to generate a pulsed acoustic signal.

11. A particle sensor as claimed in claim 10 wherein the pulsing means includes means for pulsing the acoustic beacon means at two or more different frequencies to indicate different conditions of the particle sensor.

12. A particle sensor as claimed in claim 11 wherein the pulsing means includes means for sensing an abnormal condition to pulse the acoustic beacon means at a frequency different from a pulse frequency indicating a normal condition.

13. A particle sensor as claimed in claim 10 including means for overriding the pulsing means to operate the acoustic beacon means continuously in response to a condition of the particle sensor.

14. A particle sensor as claimed in claim 13 wherein the overriding means includes a tilt sensing switch to detect a tilting of the particle sensor to continuously operate the acoustic beacon means.

15. A particle sensor as claimed in claim 8 including first battery means for supplying operating power to the sensing means and the recording means, and second battery means for supplying power to the beacon means.

16. A particle sensor as claimed in claim 8 wherein the housing includes upper, middle and lower sections and means for sealing the lower and middle sections from each other and the upper section, said sensing means is enclosed in the lower section, said beacon means is mounted in the upper section, and there is further included battery means mounted in the middle section for the electronic circuit.

17. A particle sensor as claimed in claim 16 wherein the housing is formed from a pipe with bottom and top caps, said top cap and upper section having perforations for permitting acoustic transmission from the beacon means while the beacon means is protected by the housing.

18. A particle sensor as claimed in claim 8 further including a temperature sensor, and a pressure sensor.

19. A particle sensor comprising:
    a tubular sealed housing formed from a vibration-transmitting structural material which is resistant to mechanical failure from particle impingement and detrimental environmental conditions when placed vertically in a stream with a bottom end of the housing embedded in a bed of the stream, an electro-mechanical transducer contained within the housing and mechanically coupled to the housing for converting vibrations of the housing to electrical signal, an electronic circuit contained in the housing and electrically coupled to the electro-mechanical transducer for detecting oscillatory events in the electrical signals corresponding to particle impingement, recording means contained within the housing and coupled to the electronic circuit for recording data of the oscillatory events, and a long brightly colored buoyant pennant attached to the housing for enabling visual relocation when the sensor is displaced.

20. A particle sensor as claimed in claim 19 including acoustic beacon means mounted on the housing for emitting an acoustic signal.

21. A particle sensor as claimed in claim 20 further including a tilt sensing switch to detect a tilting of the particle sensor to continuously operate the acoustic beacon means.

* * * * *